United States Patent
Imig et al.

(10) Patent No.: US 7,550,617 B2
(45) Date of Patent: Jun. 23, 2009

(54) COMPOSITIONS AND METHODS FOR THE TREATMENT OF RENAL AND CARDIOVASCULAR DISEASE

(75) Inventors: John D. Imig, Evans, GA (US); John R. Falck, University Park, TX (US)

(73) Assignees: Medical College of Georgia Research Institute, Augusta, GA (US); Board of Regents, The University of Texas System, Austin, TX (US)

( * ) Notice: Subject to any disclaimer, the term of this patent is extended or adjusted under 35 U.S.C. 154(b) by 1 day.

(21) Appl. No.: 11/866,395

(22) Filed: Oct. 2, 2007

(65) Prior Publication Data

US 2008/0146663 A1 Jun. 19, 2008

Related U.S. Application Data

(60) Provisional application No. 60/848,708, filed on Oct. 2, 2006.

(51) Int. Cl.
*A23D 9/00* (2006.01)
(52) U.S. Cl. .................. 554/224; 560/186; 560/179; 562/553; 514/546; 514/563
(58) Field of Classification Search ............ 554/224; 514/546, 563; 560/186, 179; 562/553
See application file for complete search history.

(56) References Cited

U.S. PATENT DOCUMENTS

| 6,890,925 | B2 | 5/2005 | Ingraham et al. |
| 2006/0148744 | A1 | 7/2006 | Hammock et al. |

OTHER PUBLICATIONS

Falck et al., "11,12-Epoxyeicosatrienoic Acid (11,12-EET): Structural Determinants for Inhibition of TNF-alpha-Induced VCAM-1 Expression," Bioorganic & Medicinal Chemistry Letters 13, 2003, 4011-4014.

Imig et al., "Enhanced renal microvascular reactivity to angiotensin II in hypertension is ameliorated by the sulfonimide analog of 11,12-epoxyeicosatrienoic acid," Journal of Hypertension, 2001, 19:983-992.

Imig, "Epoxide hydrolase and epoxygenase metabolites as therapeutic targets for renal diseases," Am J Physiol Renal Physiol, 2005, 289:F496-F503.

Zhao et al., "Decreased Renal Cytochrome P450 2C Enzymes and Impaired Vasodilation Are Associated With Angiotensin Salt-Sensitive Hypertension," Hypertension, 2003, 41:709-714.

*Primary Examiner*—Deborah D Carr
(74) *Attorney, Agent, or Firm*—Sutherland Asbill & Brennan LLP

(57) ABSTRACT

Derivative compounds of 11-nonyloxy-undec-8(Z)-eonic acid that mimic epoxide metabolites are provided. Also provided are compositions comprising a therapeutically effective amount of the derivative compounds. The present invention further provides methods for the use of such compositions for the treatment of renal or cardiovascular disease and/or related conditions.

27 Claims, 9 Drawing Sheets

COMPOSITIONS AND METHODS FOR THE TREATMENT OF RENAL AND CARDIOVASCULAR DISEASE

CROSS-REFERENCE TO RELATED APPLICATIONS

This application claims priority to U.S. Provisional Application Ser. No. 60/848,708 filed Oct. 2, 2006, the entire content of which is hereby incorporated in its entirety.

ACKNOWLEDGMENT OF FEDERAL RESEARCH SUPPORT

This invention was made, at least in part, with funding from National Institutes of Health (NIH Grant Numbers HL-59699 and DK-38226 to JI). Accordingly, the United States Government has certain rights in this invention.

BACKGROUND OF THE INVENTION

1. Field of the Invention

This invention relates generally to compositions and methods for the treatment of renal and cardiovascular diseases. In particular, this invention relates to compositions comprising compounds that mimic epoxide metabolites and to methods for the use of such compositions for the treatment of renal or cardiovascular disease and/or related conditions.

2. Background Art

A major cause of morbidity and mortality is the progression of organ damage associated with renal and cardiovascular diseases. The incidence of end-stage renal disease (ESRD) is escalating, and the two main diseases responsible for the increase in ESRD are diabetes and hypertension. In the case of diabetes, unused glucose remaining in the blood damages the nephrons, resulting in diabetic nephropathy. In patients with hypertension, small blood vessels in the kidney may become damaged and then cannot function properly to filter wastes. One contributing factor to end-organ damage is an impaired endothelium. Interestingly, endothelial dysfunction has been touted as a marker for unfavorable cardiovascular prognosis in humans.

Earlier studies have shown that endothelium-derived factors can act on vascular smooth muscle cells to relax or contract arteries. Nitric oxide and prostaglandins are the main products of the endothelial cells that relax the vascular smooth muscle. In addition, the endothelium releases one or more substances that relax vascular smooth muscle cells through membrane hyperpolarization (i.e., endothelium-derived hyperpolarizing factors (EDHFs)). A number of studies have provided evidence that this nitric oxide- and cyclooxygenase (COX)-independent endothelium-derived relaxing factor is a metabolite of the arachidonic acid cascade. It has been postulated that the unidentified EDHF hyperpolarized vascular smooth muscle cells by activating calcium-activated $K^+$ channels ($K_{Ca}$), but the identity of the EDHF(s) has been debated.

Cytochrome P-450 (CYP) metabolites produced by the endothelium have been shown to have antihypertensive properties. Epoxyeicosatrienoic acids (EETs) are produced by the kidney and act to increase renal blood flow and promote sodium secretion. It has been proposed that the EETs are the endothelium-derived hyperpolarizing factors (EDHFs). Additionally, EETs have been demonstrated to have profibrinolytic effects, to have anti-inflammatory actions, and to inhibit smooth vascular muscle cell migration. The corresponding diols, dihydroxyeicosatrienoic acids (DHETEs), lack renal vascular dilator activity. DHETEs are generated from EETs by the action of a soluble epoxide hydrolase (SHE), and in a number of vascular systems, the diols either have decreased actions or are devoid of activity.

Several EETs have been analyzed with respect to their ability to function as an EDHF. In particular, 5,6-EET is an EDHF candidate because it decreases renal perfusion pressure in the Wistar-Kyoto and spontaneously hypertensive (SHR) rats. In addition, 11,12-EET and 14,15-EET are the two epoxide metabolites of arachidonic acid that most consistently demonstrate vascular smooth muscle cell-relaxing properties and other cardiovascular protective activities. 11,12-EET acts on preglomerular vascular smooth muscle cells to dilate the arteriole. In addition, this epoxide metabolite activates renal microvascular smooth muscle cell $K_{Ca}$ channels and activates $K_{Ca}$ channels in cerebral and coronary vascular smooth muscle cells as well. ADP ribosylation is one intracellular mechanism that has been demonstrated to activate $K_{Ca}$ channels in coronary arteries. In addition, epoxides also have been shown to hyperpolarize platelets by activating $K_{Ca}$ channels. Renal microvascular activation of $K_{Ca}$ channels appears to be mediated by cAMP stimulation of protein kinase A because afferent arteriolar dilation to the sulfonamide analog of 11,12-EET was substantially reduced by protein kinase A inhibition. The $K_{Ca}$ channel- and protein kinase A-mediated dilator actions of 11,12-EET on afferent arterioles are consistent with the concept that 11,12-EET is an EDHF. Besides arterial endothelial cells, epoxyeicosatrienoic acid (EET) generation has been demonstrated in brain astrocytes, cardiac myocytes, airway tissues, the gastrointestinal tract, pancreas, and kidney. Vasodilation to EETs has been observed in renal, mesenteric, cerebral, pulmonary, and coronary arteries Abnormal regulation of kidney and vascular epoxide metabolites occurs in renal and cardiovascular diseases including, for example, type 1 and type 2 diabetes, heptorenal syndrome, metabolic syndrome, insulin resistance syndrome, glomerullonephritis, hypertension, congestive heart failure, heart attack, hypertensive heart disease, atherosclerosis, coronary artery disease, angina, ischemia, ischemic stroke, Raynaud's disease, and renal disease. The protective actions of the epoxide metabolites are diminished or lost in these disease states.

To date, various strategies have been employed for the treatment of renal and/or cardiovascular disease. For example, some researchers have focused on the role of soluble epoxide hydrolase (SEH) in renal and cardiovascular disease and inhibition of this enzyme as an avenue to increase EET levels. See, e.g., U.S. Pat. No. 6,890,925 Ingraham et al.; U.S. Publication No. 2006/0148744; and Imig, 2005, 289: F496-F503. Although some methods have been achieved which effectively treat renal and cardiovascular disease, clearly more therapeutics are needed to treat a broader range of renal and/or cardiovascular diseases and conditions, as well as to increase the efficacy of the methods that already exist.

Therefore, what is needed in the art are new compounds and compositions for treating renal and/or cardiovascular diseases and conditions. What is also needed are methods for treating renal and/or cardiovascular diseases and conditions such as type 1 and type 2 diabetes, heptorenal syndrome, metabolic syndrome, insulin resistance syndrome, glomerullonephritis, hypertension, congestive heart failure, heart attack, hypertensive heart disease, atherosclerosis, coronary artery disease, angina, ischemia, ischemic stroke, Raynaud's disease, and renal disease.

SUMMARY OF THE INVENTION

This invention fulfills in part the need to identify new, unique compounds, pharmaceutical compositions, and methods for treating renal and cardiovascular disease. In particular, the present invention describes compounds that are derivatives of 11-nonyloxy-undec-8(Z)-eonic acid that decrease blood pressure in an art-accepted animal model for hypertension. These and other embodiments of the invention will become apparent to one of skill in the art upon review of the description of the invention.

The invention provides compounds that are derivatives of 11-nonyloxy-undec-8(Z)-eonic acid or a pharmaceutically acceptable salt thereof, wherein the compound reduces blood pressure. In a preferred embodiment, the compound has the structural formula (I):

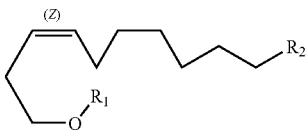

or a pharmaceutically acceptable salt or derivative thereof, wherein $R_1$ is selected from the group consisting of a $C_{6-9}$ alkyl, branched alkyl, or cycloalkyl; and $R_2$ is selected from the group consisting of:

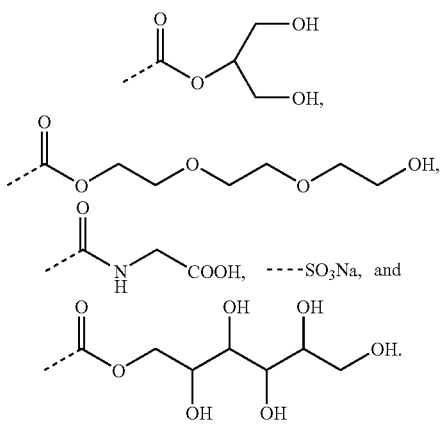

The invention also provides compositions comprising a therapeutically effective amount of a derivative of 11-nonyloxy-undec-8(Z)-eonic acid or a pharmaceutically acceptable salt or derivative thereof, wherein the compound reduces blood pressure.

DETAILED DESCRIPTION OF THE INVENTION

Figure 1A:
FIG. 1A shows the effect of Ether-EET (11-nonyloxy-undec-8(Z)-enoic acid) on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1A:
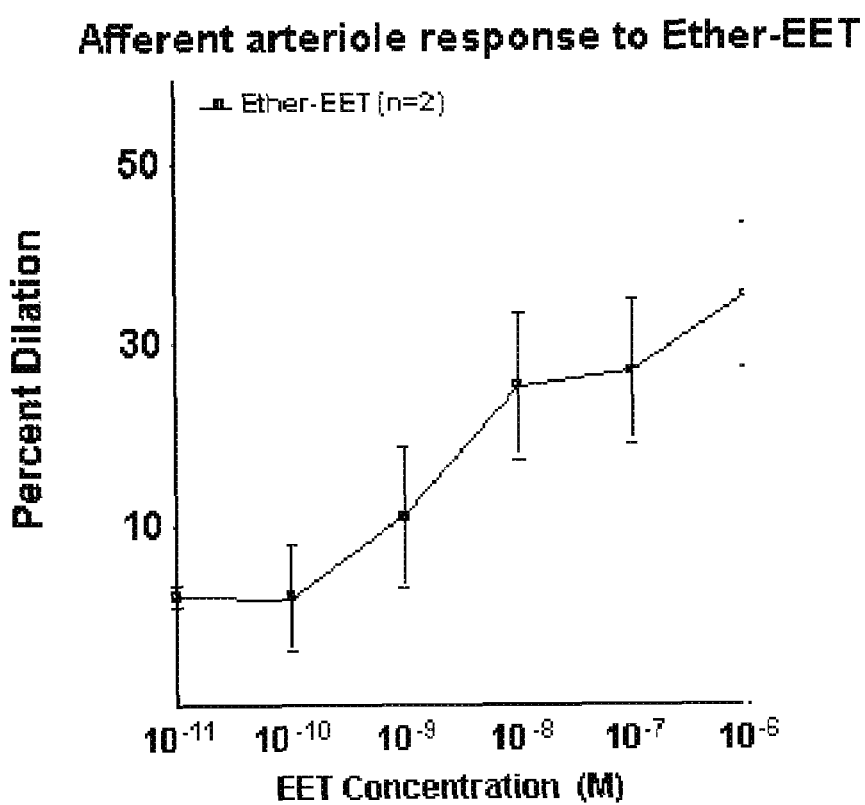

The present invention may be understood more readily by reference to the following detailed description of the preferred embodiments of the invention and the Examples included herein. However, before the present methods are disclosed and described, it is to be understood that this invention is not limited to the specific compounds, specific compositions, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. It is further to be understood that unless specifically defined herein, the terminology used herein is to be given its traditional meaning as known in the relative art.

As used in the specification and the appended claims, the singular forms "a," "an," and "the" include plural forms unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The present invention describes for the first time that the disclosed epoxide metabolite derivatives are useful to increase renal blood flow and to promote sodium secretion. It has been proposed that the epoxide metabolite EETs are the endothelium-derived hyperpolarizing factors (EDHFs). Additionally, EETs have been demonstrated to have profibrinolytic effects, to have anti-inflammatory actions, and to inhibit smooth vascular muscle cell migration.

The invention provides compounds that are derivatives of 11-nonyloxy-undec-8(Z)-eonic acid or a pharmaceutically acceptable salt thereof, wherein the compound reduces blood pressure. In a preferred embodiment, the compound has the structural formula (I):

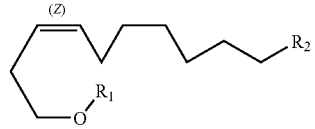

or a pharmaceutically acceptable salt or derivative thereof, wherein $R_1$ is selected from the group consisting of a $C_{6-9}$ alkyl, branched alkyl, or cycloalkyl; and $R_2$ is selected from the group consisting of:

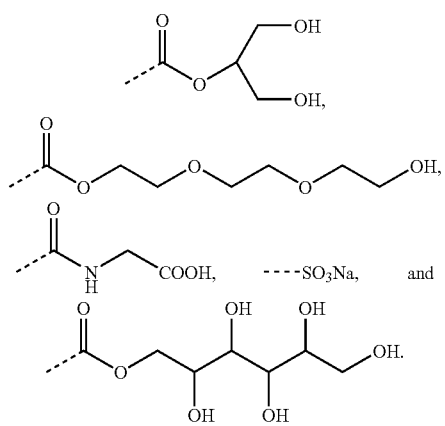

In another preferred embodiment the compound is selected from the group consisting of:

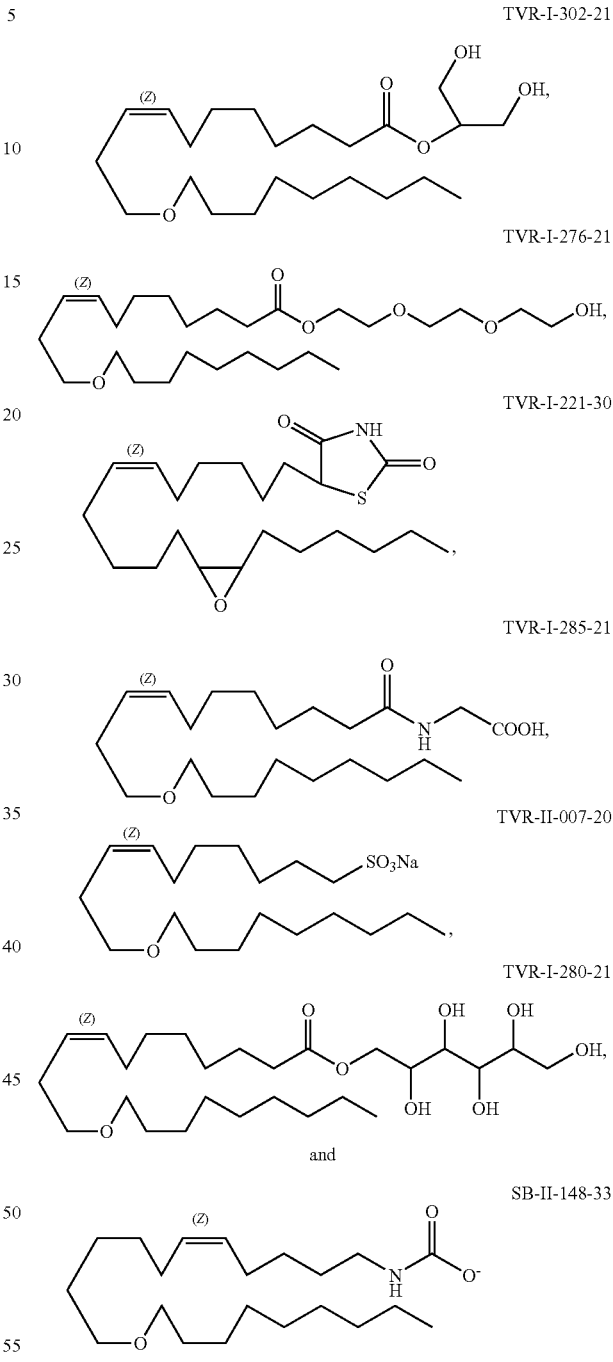

or the pharmaceutically acceptable salts or derivatives thereof.

Any of the compounds of formula I containing one or more asymmetric carbon atoms may occur as racemates and racemic mixtures, single enantiomers, diastereomeric mixtures, or individual diastereomers. All such isomeric forms of these compounds are expressly included in the present invention. Each stereogenic carbon may be in the R or S configuration, or a combination of configurations. Some of the compounds of formula I can exist in more than one tautomeric form. The invention includes use of all such tautomers.

The compounds of formula I are only those which are contemplated to be "chemically stable" as will be appreciated by those skilled in the art. For example, compounds which would have a "dangling valency," or a "carbanion" are not compounds contemplated to be used in the methods of the invention.

All alkyl, alkylene, alkenyl, alkenylene, alkynyl, and alkynylene groups shall be understood as being $C_{1-10}$, branched or unbranched unless otherwise specified. As used herein, the phrase "pharmaceutically acceptable salt or derivative" includes any pharmaceutically acceptable salt or ester of a compound of this invention, or any other compound which, upon administration to a patient, is capable of providing (directly or indirectly) a compound used in this invention, a pharmacologically active metabolite, or pharmacologically active residue thereof.

In another embodiment, the compound has the structural formula (I):

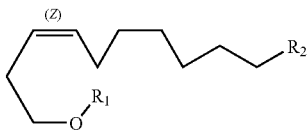

or a pharmaceutically acceptable salt or derivative thereof, wherein $R_1$ is selected from the group consisting of an alkyl, branched alkyl, and cycloalkyl; and $R_2$ is selected from the group consisting of an alkyl, branched alkyl, cycloalkyl, alkyloxy, alkylthio, alkylamino, alkyloxyalkyl, alkylthioalkyl, alkylaminoalkyl, dialkylaminoalkyl, alkenyl, branched alkenyl, carbocyclyl, or heterocyclyl each optionally substituted with one or more halogen, CN, $NO_2$, $SO_3$alkyl, alkylthio, alkylsulfinyl, and alkylsulfonyl.

The present invention also provides pharmaceutical compositions comprising a therapeutically effective amount of a compound that is a derivative of 11-nonyloxy-undec-8(Z)-eonic acid or a pharmaceutically acceptable salt thereof, wherein the compound reduces blood pressure. In a preferred embodiment, the compound has the structural formula:

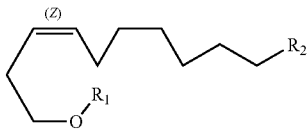

or a pharmaceutically acceptable salt or derivative thereof, wherein $R_1$ is selected from the group consisting of a $C_{6-9}$ alkyl, branched alkyl, or cycloalkyl; and $R_2$ is selected from the group consisting of:

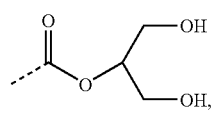

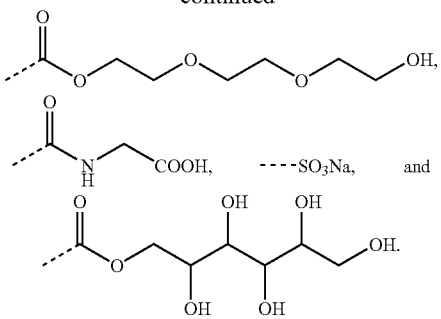

In another preferred embodiment, the pharmaceutical compositions of the present invention comprise a therapeutically effective amount of a compound selected from the group consisting of:

(Z)-1,3-dihydroxypropan-2-yl 11-(nonyloxy)undec-8-enoate, (Z)-2-(2-(2-hydroxyethoxy)ethoxy)ethyl 11-(nonyloxy)undec-8-enoate, (Z)-2-(11-(nonyloxy)undec-8-enamido)acetic acid, sodium (Z)-10-(nonyloxy)dec-7-ene-1-sulfonate, (Z)-2,3,4,5,6-pentahydroxyhexyl 11-(nonyloxy)undec-8-enoate, (Z)-5-(11-(3-hexyloxiran-2-yl)undec-6-enyl)thiazolidine-2,4-dione, and (Z)-14-(hexyloxy)tetradec-5-enoate.

The present invention also provides methods for treating a renal or cardiovascular disease, said method comprising administering to a patient in need thereof a therapeutically effective amount of a compound that is a derivative of 11-nonyloxy-undec-8(Z)-eonicacid or a pharmaceutically acceptable salt thereof, wherein the compound reduces blood pressure. In a preferred embodiment the compound has the structural formula:

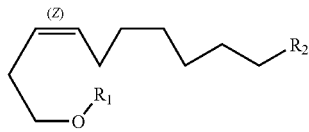

or a pharmaceutically acceptable salt thereof, wherein $R_1$ is selected from the group consisting of a $C_{6-9}$ alkyl, branched alkyl, or cycloalkyl; and $R_2$ is selected from the group consisting of:

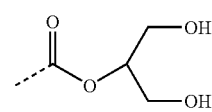

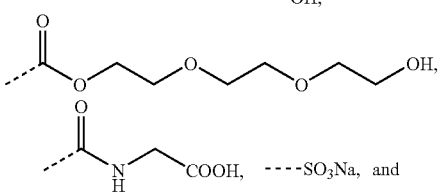

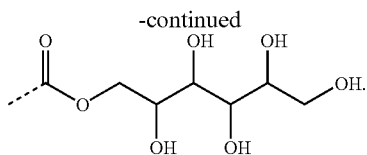

In another preferred embodiment, the methods for treating a renal or cardiovascular disease comprises administering to a patient in need thereof a therapeutically effective amount of a compound selected from the group consisting of:
(Z)-1,3-dihydroxypropan-2-yl 11-(nonyloxy)undec-8-enoate,
(Z)-2-(2-(2-hydroxyethoxy)ethoxy)ethyl 11-(nonyloxy)undec-8-enoate,
(Z)-2-(11-(nonyloxy)undec-8-enamido)acetic acid,
sodium (Z)-10-(nonyloxy)dec-7-ene-1-sulfonate,
(Z)-2,3,4,5,6-pentahydroxyhexyl 11-(nonyloxy)undec-8-enoate,
(Z)-5-(11-(3-hexyloxiran-2-yl)undec-6-enyl)thiazolidine-2,4-dione, and
(Z)-14-hexyloxy)tetradec-5-enoate.

In certain preferred embodiments of the present invention, the methods for treating renal or cardiovascular disease are used to treat a patient with a disease or condition selected from a group consisting of, but not limited to, type 1 and type 2 diabetes, heptorenal syndrome, metabolic syndrome, insulin resistance syndrome, glomerulonephritis, hypertension, congestive heart failure, heart attack, hypertensive heart disease, atherosclerosis, coronary artery disease, angina, ischemia, ischemic stroke, Raynaud's disease, and renal disease.

In certain other embodiments of the present invention, the methods further comprise administering to the patient a therapeutically effective amount of an additional agent that is used to treat renal and/or cardiovascular disease. As used herein, a "therapeutically effective amount" is an amount which increases renal blood flow, promotes sodium secretion, has a profibrinolytic effect, has an anti-inflammatory effect, and/or inhibits smooth vascular muscle cell migration. As also used herein, an "additional agent that is used to treat renal and/or cardiovascular disease" refers to a molecule which increases renal blood flow, promotes sodium secretion, has a profibrinolytic effect, has an anti-inflammatory effect, and/or inhibits smooth vascular muscle cell migration. In certain embodiments, the additional agent is selected from the group consisting of alpha blockers, angiotensin-converting enzyme (ACE) inhibitors, angiotensin receptor blockers (ARBs), beta-blockers, calcium channel blockers, central alpha agonists, diuretics, renin inhibitors, including aliskiren, vasodilators, clonidine, diazoxide, furosemide, hydralazine, minoxidil, and nitroprusside.

Another aspect of the invention pertains to the use of isolated epoxide derivative compounds. An "isolated" or "purified" epoxide derivative compound or biologically active portion thereof is "substantially free of chemical precursors or other chemicals." This includes preparations of the epoxide derivative compound in which the compound is separated from chemical precursors or other chemicals that are involved in the synthesis of the derivative compound. In one embodiment, the language "substantially free of chemical precursors or other chemicals" includes preparations of an epoxide derivative having less than about 30% (by dry weight) of chemical precursors or other chemicals, more preferably less than about 20% chemical precursors or other chemicals, still more preferably less than about 10% chemical precursors or other chemicals, and most preferably less than about 5% chemical precursors or other chemicals.

The compositions of this invention further comprise a pharmaceutically acceptable carrier. The phrases "pharmaceutically or pharmacologically acceptable" refer to molecular entities and compositions that do not produce an adverse, allergic, or other untoward reaction when administered to an animal, or a human, as appropriate. Veterinary uses are equally included within the invention and "pharmaceutically acceptable" formulations include formulations for both clinical and/or veterinary use. As used herein, "pharmaceutically acceptable carrier" includes any and all solvents, dispersion media, coatings, antibacterial, and antifungal agents, isotonic and absorption delaying agents, and the like. The use of such media and agents for pharmaceutically active substances is well known in the art. Except insofar as any conventional media or agent is incompatible with the active ingredient, its use in the therapeutic compositions is contemplated. For human administration, preparations should meet sterility, pyrogenicity, and general safety and purity standards as required by FDA Office of Biologics standards. Supplementary active ingredients can also be incorporated into the compositions.

As used herein with respect to these methods, the term "administering" refers to various means of introducing a composition into a cell or into a patient. These means are well known in the art and may include, for example, injection; tablets, pills, capsules, or other solids for oral administration; nasal solutions or sprays; aerosols, inhalants; topical formulations; liposomal forms; and the like. As used herein, the term "effective amount" or "therapeutically effective amount" refers to an amount that will result in the desired effect and may readily be determined by one of ordinary skill in the art.

The compositions of the present invention may be formulated for various means of administration. As used herein, the term "route" of administration is intended to include, but is not limited to subcutaneous injection, intravenous injection, intraocular injection, intradermal injection, intramuscular injection, intraperitoneal injection, intratracheal administration, epidural administration, inhalation, intranasal administration, oral administration, sublingual administration, buccal administration, rectal administration, vaginal administration, and topical administration. The preparation of an aqueous composition that contains the desired epoxide metabolite derivative compound as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The compositions of the present invention can be formulated into a sterile aqueous composition in a neutral or salt form. Solutions as free base or pharmacologically acceptable salts can be prepared in water suitably mixed with a surfactant, such as hydroxypropylcellulose. "Pharmaceutically acceptable salts" include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars, or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate, and gelatin.

Prior to or upon formulation, the compositions of the present invention should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filter sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the active compound admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that for human administration, preparations should meet sterility, pyrogenicity, and general safety and purity standards as required by FDA Office of Biological Standards.

Throughout this application and the priority application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Synthesis of 11-nonyloxy-8(Z)-enoic Acid

The compound 11-nonyloxy-8(Z)-enoic acid (Ether-EET) was synthesized as described previously (Falck et al., 2003, Bioorg. Med. Chem. Lett. 13:4011-14)(See below).

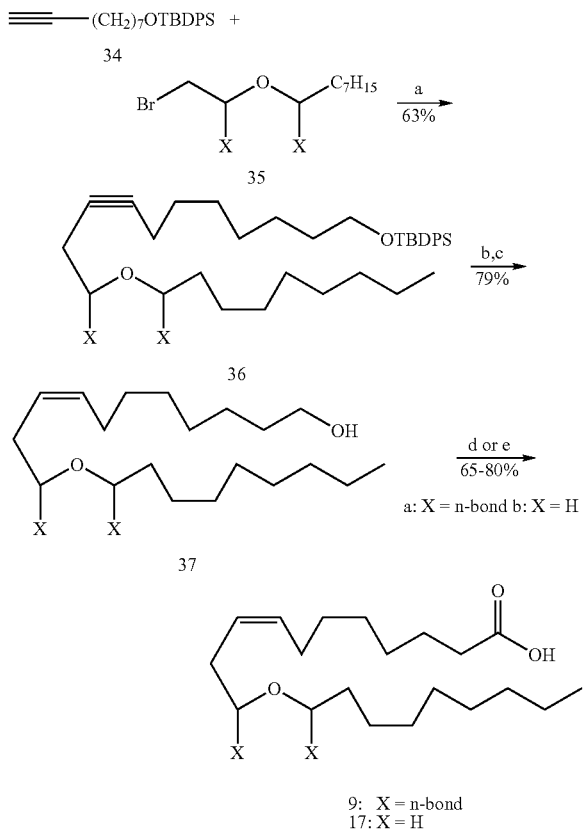

The Ether-EET analogue was synthesized: (a) n-BuLi, THF/HMPA (4:1), −40° C., 2 hours; bromide, −40° C. to room temperature, 2 hours; (b) n-BU$_4$NF, THF, 0° C., 4 hours; (c) P-2 Ni/H$_2$, EtOH, room temperature, 2 hours; (d) PDC, DMF, room temperature, 16 hours; (e) Jones reagent, acetone, −20° C., 4 hours.

The chemical synthesis of Ether-EET as shown above is indicative of the approach used for the seven 11-nonyloxy-8(Z)-enoic acid derivatives ((Z)-1,3-dihdroxypropan-2-yl 11-(nonyloxy)undec-8-enoate (TVR-I-302-21), (Z)-2-(2-(2-hydroxyethoxy)ethoxy)ethyl 11-(nonyloxy)undec-8-enoate (TVR-I-276-21), (Z)-2-(11-(nonyloxy)undec-8-enamido) acetic acid (TVR-I-221-30), (Z)-(10-(nonyloxy)dec-7-ene- 1-sulfonate (TVR-I-285-21), (Z)-2,3,4,5,6-pentahydroxyhexyl 11-(nonyloxy)undec-8-enoate (TVR-II-007-20), (Z)-5-(11-(3-hexyl oxiran-2-yl)undec-6-enyl)thiazolidine-2,4-dione (TVR-I-280-21), (Z)-14-(hexyloxy)tetradec-5-enoate (SB-II-148-33).

Example 2

Effect of Epoxide Metabolite Derivatives on Angiotensin II Infused Hypertension

Mate Sprague-Dawley rats (Charles River Laboratories, Wilmington, Mass., USA) were housed separately in cages and maintained under temperature-and light-controlled conditions. Throughout the experiments, animals had free access to standard rat chow. Surgical procedures were performed on pentobarbital (40 mg/kg body weight, i.p.) anaesthetized animals using sterile procedures. Rats weighing 180-200 g were divided into two experimental groups: one group received sham surgery, and a second group was subjected to angiotensin II infusion. Angiotensin II was infused at a continuous rate via an osmotic minipump (60 ng/min; model 2002, ALZA Corp. Palo Alto, Calif., USA) implanted subcutaneously at the dorsum of the neck. Systolic blood pressure was measured in conscious rats by tail-cuff plethysmography to monitor the progression of hypertension.

Experiments were performed using the in vitro perfused juxtamedullary nephron technique on rats 12-14 days after surgical manipulations. Animals were anaesthetized with sodium pentobarbital; the right carotid artery was cannulated; and a midline abdominal incision was made. The right renal artery was cannulated via the superior mesenteric artery, and perfusion of the kidney was immediately initiated. The kidney was perfused with a Tyrode solution containing 6% albumin and a mixture of 1-amino acids. Blood was collected through the carotid artery cannula into a heparinized saline syringe (2000 U). Erythrocytes were separated from plasma and leukocytes by centrifugation, as previously described (Imig and Deichmann, 1997, Renal Physiol. 273:F274-282). The supernatant was removed and washed twice with 0.9% NaCl containing 0.2% dextrose (pH 7.0). The red blood cells were added to a Tyrode solution containing 6% albumin to attain a haematocrit of 20% . The solution was filtered and stirred continuously in a closed reservoir that was pressurized by a 95% O2 to 5% CO2 tank. After collection of the blood, the kidney was removed from the rat and maintained in an organ chamber at room temperature throughout the isolation and dissection procedure. The juxtamedullary vasculature was isolated as previously described (Imig and Deichmann, 1997). Upon completion of the microdissection procedures, the Tyrode solution was replaced by the blood solution, and renal artery perfusion pressure measured at the tip of the cannula was set to 100 mmHg. The organ chamber and bathing solution were warmed to 37° C., and the tissue surface was continuously superfused with a Tyrode solution containing 1% albumin.

Afferent arteriolar diameters were measured via video microscopy techniques. The isolated kidney was trans-illuminated on the fixed stage of a microscope equipped with a 75-W xenon lamp and a 40×water immersion objective. Images of the blood vessel under study were captured by a Newvicon camera, passed through a time-date generator and image enhancing system, displayed on a monitor, and videotaped for later analysis. Vessel diameter was measured using a digital image-shearing monitor that was calibrated by a stage micrometer and measurements were reproducible within 0.5 μm.

Figure 1B:
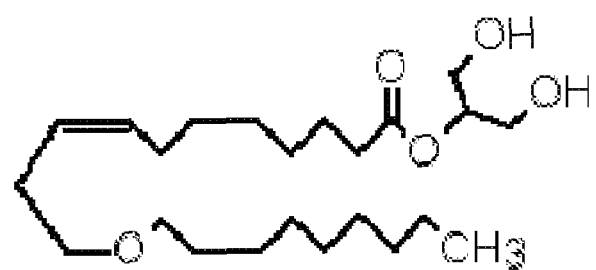
FIG. 1B shows the effect of the 11-nonyloxy-undec-8(Z)-enoic acid derivative TVR-I-302-21 on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1B:
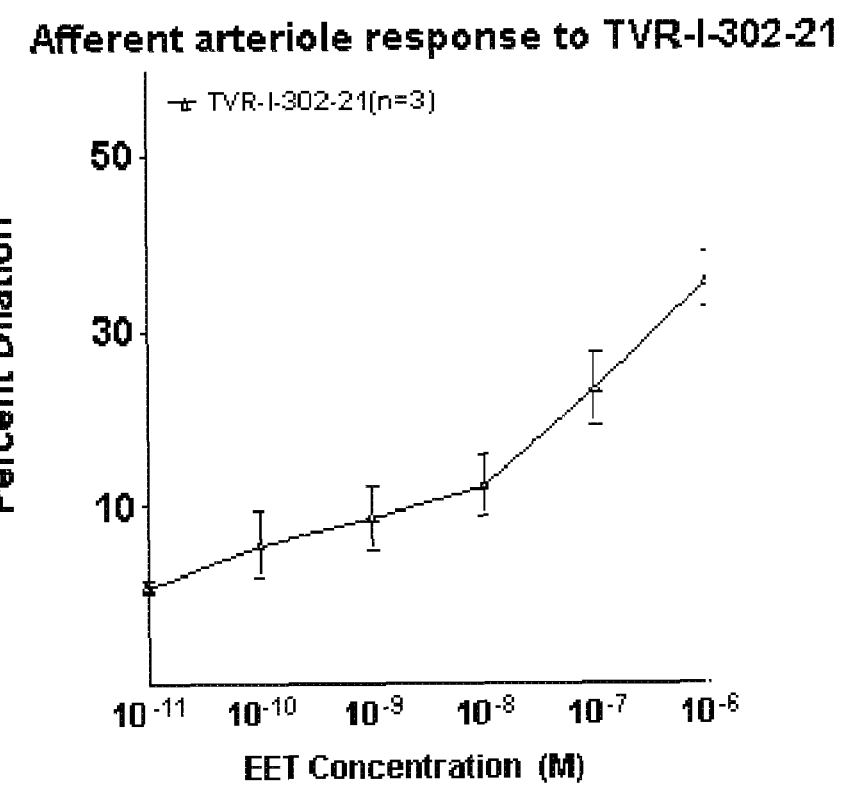
Figure 1C:
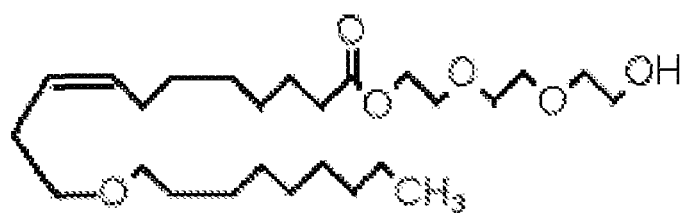
FIG. 1C shows the effect of the 11-nonyloxy-undec-8(Z)-enoic acid derivative TVR-I-276-21 on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1C:
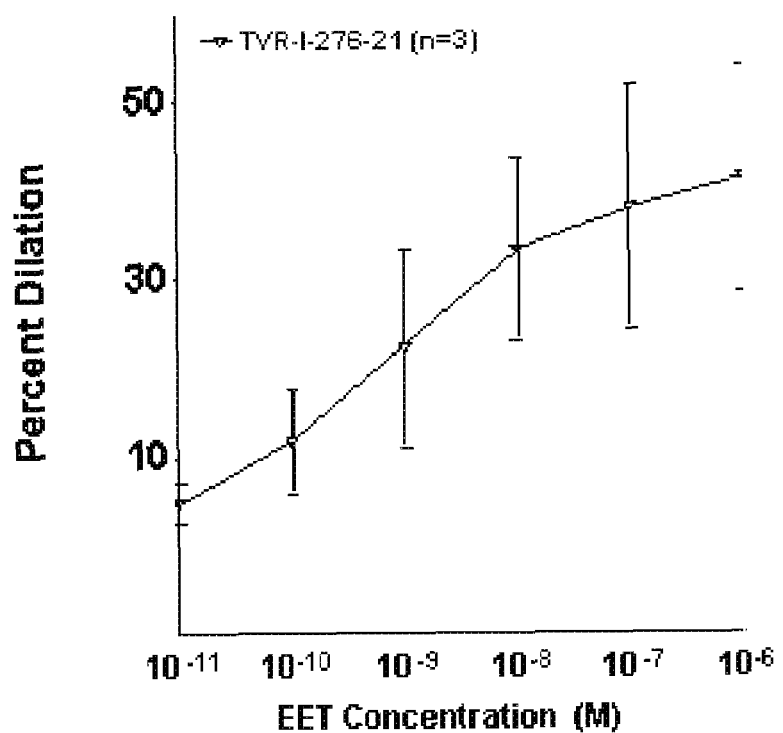
Figure 1D:
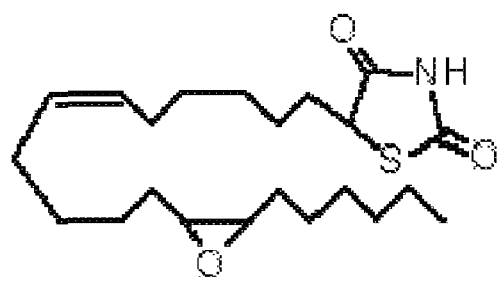
FIG. 1D shows the effect of the 11-nonyloxy-undec-8(Z)-enoic acid derivative TVR-I-221-30 on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1D:
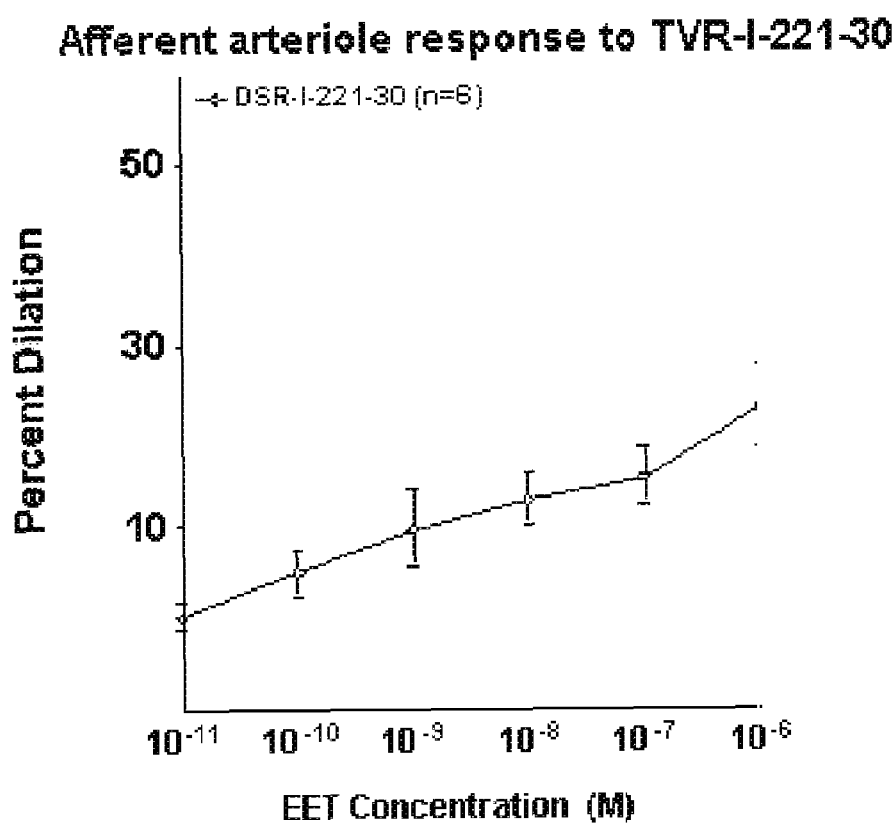
Figure 1E:
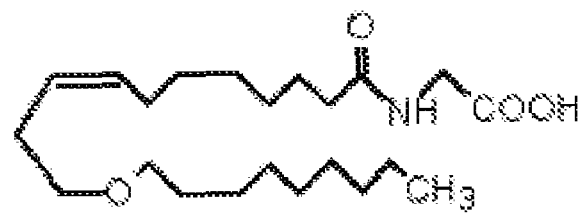
FIG. 1E shows the effect of the 11-nonyloxy-undec-8(Z)-enoic acid derivative TVR-I-285-21 on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1E:
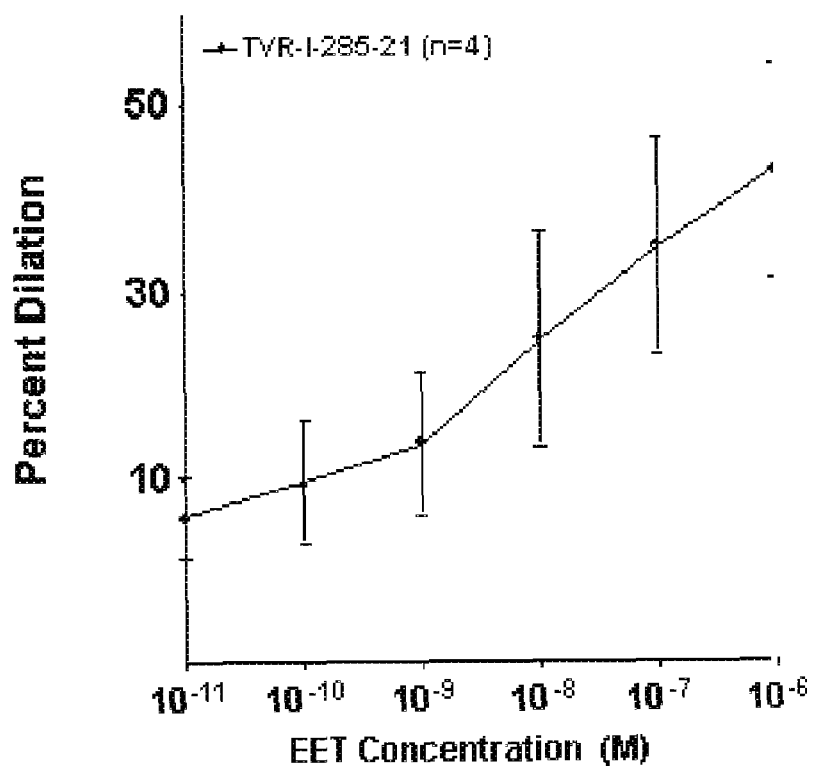
Figure 1F:
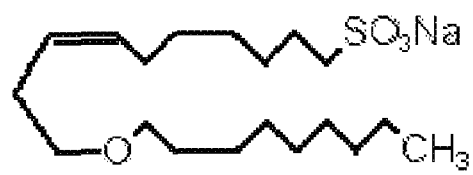
FIG. 1F shows the effect of the 11-nonyloxy-undec-8(Z)-enoic acid derivative TVR-II-007-20 on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1F:
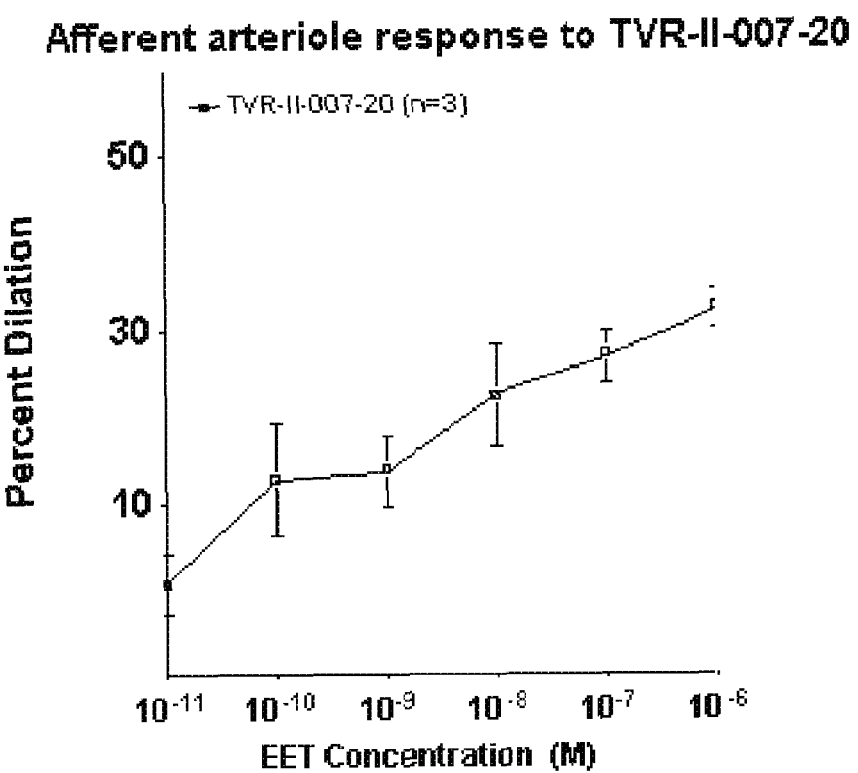
Figure 1G:
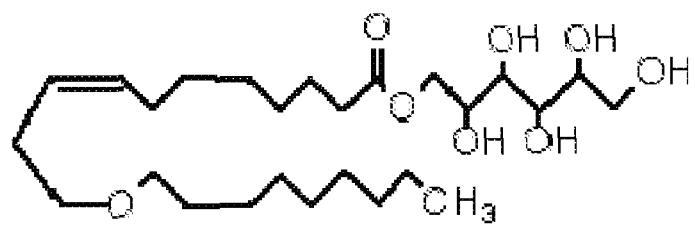
FIG. 1G shows the effect of the 11-nonyloxy-undec-8(Z)-enoic acid derivative TVR-I-280-21 on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1G:
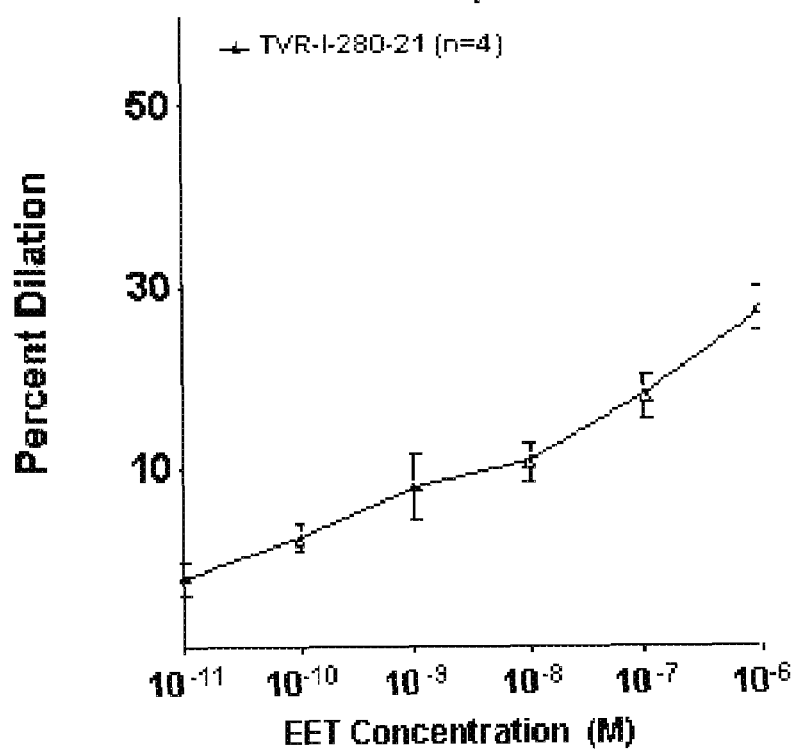
Figure 1H:
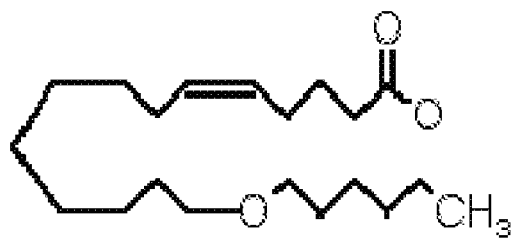
FIG. 1H shows the effect of the 11-nonyloxy-undec-8(Z)-enoic acid derivative SB-II-148-33 on the dilation of afferent arterioles in male Sprague-Dawley rats. The chemical structure of the compound tested is shown above the graph. The effect of the compound is shown in the graph, and is represented as a percent increase in the dilation of the afferent arterioles.
Figure 1H:
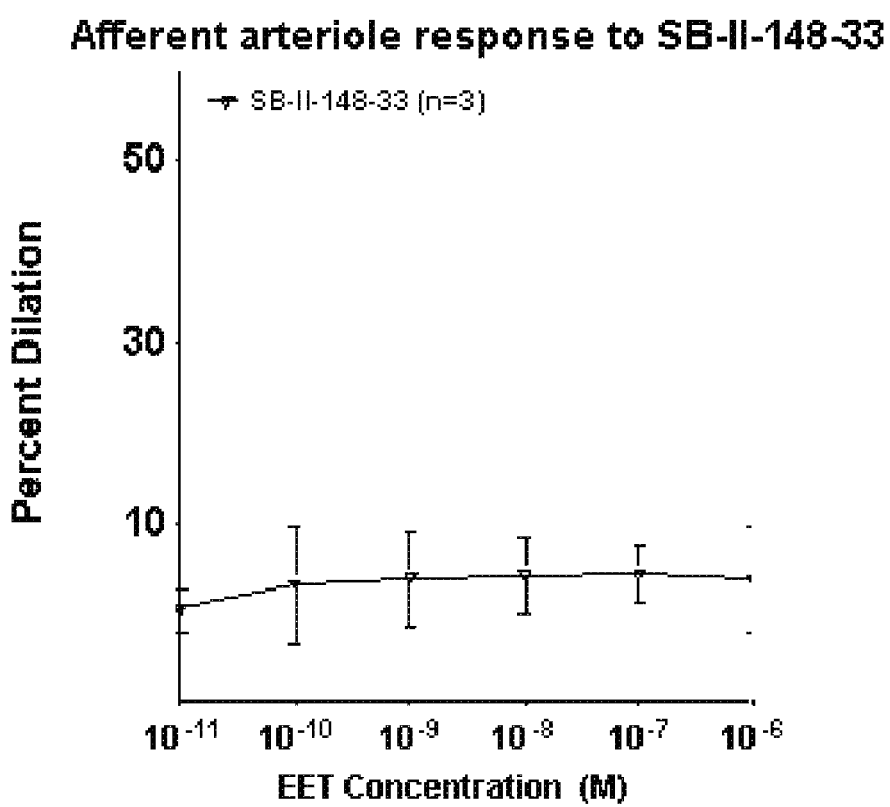
Figure 2:
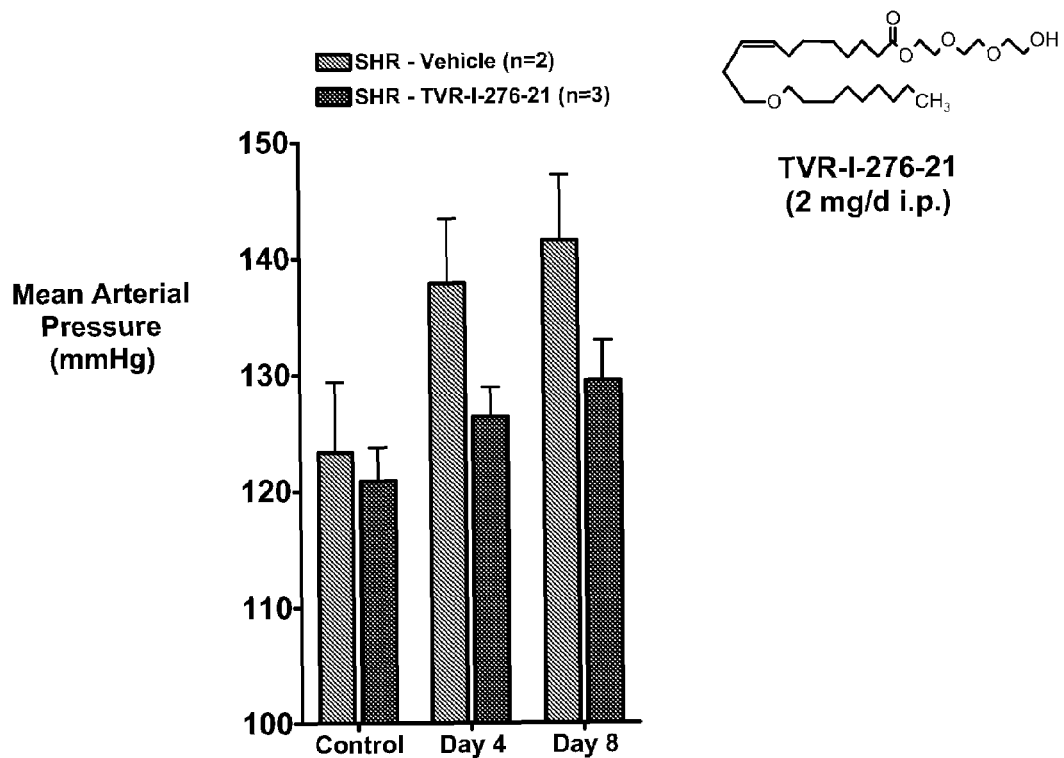
FIG. 2 shows the effect of the 11-nonyloxy-undec-8(Z)-enoic acid derivative TVR-I-276-21 on the mean arteriole pressure in spontaneously hypertensive rats (SHRs) as compared to the effect of vehicle alone. The chemical structure of the compound tested is shown above the graph. The effect of the compound is shown in the bar graph, and is represented as the mean arteriole pressure (mmHg).

After an equilibration period, the proximal portion of two to six afferent arterioles were chosen for study of each compound's effect. Measurements of afferent arteriolar diameter were made for a 5 minute period at a site at least 50 μm from any branch point. The control vascular diameter at a renal perfusion pressure of 100 mmHg over a 5 minute period was determined. Norepinephrine (0.5 μmol/l, Sanofi/Winthrop Pharmaceuticals, San Diego, Calif., USA) was added to the perfusate to elevate basal tone. Following norepinephrine treatment, the afferent arteriole response to superfusion of the epoxide metabolite compounds was determined at varying concentrations. The superfusate was returned to the control solution for 10 minutes, and vessel diameter was allowed to recover. Renal perfusion pressure was then increased to 150 mmHg, and the response to superfusion of the epoxide metabolite compounds was determined again. Steady-state diameter was attained by the end of 2 minutes, and the average diameter at 3-5 minutes for each of the epoxide metabolite derivative compounds was utilized for statistical analysis. Each of the tested epoxide metabolite derivative compounds increased the dilation of the afferent arterioles at a rate similar to or greater than the control epoxide metabolite (FIGS. 1A-1H). The epoxide metabolite derivative compounds were synthesized as described above.

Alternative method for measurement of effect: Control afferent arteriolar diameter measurements are made at a renal perfusion pressure of 100 mmHg as described above. Angiotensin II (0.1-10 nmol/l) is subsequently delivered by superfusion for 3 minutes, and a cumulative concentration curve is obtained. The vessel is allowed to recover, and the response to angiotensin II is determined at a renal perfusion pressure of 150 mmHg. Next, renal perfusion pressure is lowered to 100 mmHg and the epoxide metabolite derivative test compound (100 nmol/l) is delivered by superfusion. Based on measured tissue and urine EET levels, as well as biological activity, it is determined whether 100 nmol/l of the test compound is within the physiological range. The afferent arteriolar response to angiotensin II is re-assessed at the two renal perfusion pressures in the continued presence of the test compound. Steady-state diameter is attained by the end of 2 minutes, and the average diameter at 3 minutes for each angiotensin II concentration is utilized for statistical analysis.

Example 3

Effect of Epoxide Metabolite Derivatives on Spontaneously Hypertensive Rat

As the 11-nonyloxy-undec-8(Z)-enoic acid derivatives lowered blood pressure in angiontensin hypertension, additional experiments were performed to determine if one of the derivatives could lower blood pressure in another hypertension model system. Male spontaneously hypertensive rats (SHRs) were maintained on a 12-hour light-dark cycle and allowed access to food and water ad libitum. These studies complied with the protocols for animal use outlined by the American Physiological Society and were approved by the institutional animal care and use committee.

Rats from 6 to 12 weeks of age were treated with 11-nonyloxy-undec-8(Z)-enoic acid derivative (TVR-I-276-21)(2 mg/d i.p.) or vehicle for 8 days. Blood pressure was measured at Day 0, Day 4, and Day 8. Blood pressure significantly increased from control levels in the SHRs that were administered vehicle. In contrast, the blood pressure of the SHRs that were treated with TVR-I-276-21 (2 mg/d i.p.) did not increase to the same extent as those that received the vehicle treatment. These data provide further evidence that 11-nonyloxy-undec-8(Z)-enoic acid derivatives can lower blood pressure in art-accepted animal model systems for hypertension.

What is claimed is:

1. An 11-nonyloxy-undec-8(Z)-eonic acid derivative compound or a pharmaceutically acceptable salt thereof. wherein the compound reduces blood pressure.

2. The compound of claim 1, wherein the compound has the structural formula:

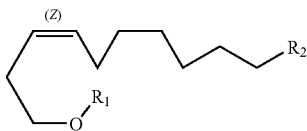

or a pharmaceutically acceptable salt thereof, wherein
R$_1$ is selected from the group consisting of a C$_{6-9}$ alkyl, branched alkyl, and cycloalkyl; and
R$_2$ is selected from the group consisting of:

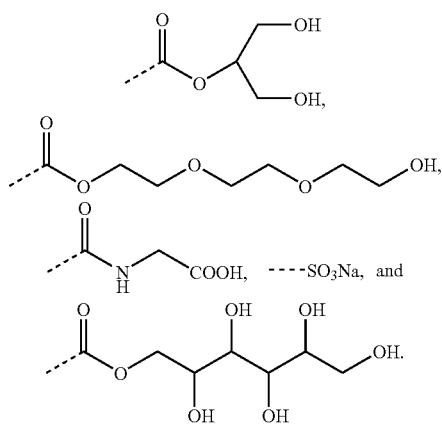

3. The compound of claim 1, wherein the compound is selected from the group consisting of:
(Z)-1,3-dihydroxypropan-2-yl1 1-(nonyloxy)undec-8-enoate,
(Z)-2-(2-(2-hydroxyethoxy)ethoxy)ethyl1 1-(nonyloxy)undec-8-enoate,
(Z)-2-(11-(nonyloxy)undec-8-enamido)acetic acid,
sodium (Z)-10-(nonyloxy)dec-7-ene-1-sulfonate, and
(Z)-2,3,4,5,6-pentahydroxyhexyl1 1-(nonyloxy)undec-8-enoate.

4. The compound of claim 3, wherein the compound is (Z)-1,3-dihydroxypropan-2-yl1 1-(nonyloxy)undec-8-enoate.

5. The compound of claim 3, wherein the compound is (Z)-2-(2-(2-hydroxyethoxy)ethoxy)ethyl1 1-(nonyloxy)undec-8-enoate.

6. The compound of claim 3, wherein the compound is (Z)-2-(11-(nonyloxy)undec-8-enamido)acetic acid.

7. The compound of claim 3, wherein the compound is sodium (Z)-10-(nonyloxy)dec-7-ene-1-sulfonate.

8. The compound of claim 3, wherein the compound is (Z)-2,3,4,5,6-pentahydroxyhexyl1 1-(nonyloxy)undec-8-enoate.

9. The compound of claim 1, wherein the compound is (Z)-5-(11-(3-hexyloxiran-2-yl)undec-6-enyl)thiazolidine-2,4-dione.

10. The compound of claim 1, wherein the compound is (Z)-14-(hexyloxy)tetradec-5-enoate.

11. A pharmaceutical composition comprising a therapeutically effective amount of a compound according to claim 1.

12. The pharmaceutical composition of claim 11, wherein the compound is selected from the group consisting of:
(Z)-1,3-dihydroxypropan-2-yl1 1-(nonyloxy)undec-8-enoate,
(Z)-2-(2-(2-hydroxyethoxy)ethoxy)ethyl1 1-(nonyloxy)undec-8-enoate,
(Z)-2-(11-(nonyloxy)undec-8-enamido)acetic acid,
sodium (Z)-10-(nonyloxy)dec-7-ene-1-sulfonate,
(Z)-2,3,4,5,6-pentahydroxyhexyl1 1-(nonyloxy)undec-8-enoate,
(Z)-5-(11-(3-hexyloxiran-2-yl)undec-6-enyl)thiazolidine-2,4-dione, and
(Z)-14-(hexyloxy)tetrade-5-enoate.

13. The pharmaceutical composition of claim 11, wherein the compound is (Z)-2-(2-(2-hydroxyethoxy)ethoxy)ethyl1 1-(nonyloxy)undec-8-enoate.

14. The pharmaceutical composition of claim 11, wherein the compound is (Z)-1,3-dihydroxypropan-2-yl1 1-(nonyloxy)undec-8-enoate.

15. The pharmaceutical composition of claim 11, wherein the compound is (Z)-2-(11-(nonyloxy)undec-8-enamido)acetic acid.

16. The pharmaceutical composition of claim 11, wherein the compound is sodium (Z)-10-(nonyloxy)dec-7-ene-1-sulfonate.

17. The pharmaceutical composition of claim 11, wherein the compound is (Z)-2,3,4,5,6-pentahydroxyhexyl1 1-(nonyloxy)undec-8-enoate.

18. The pharmaceutical composition of claim 11, wherein the compound is (Z)-5-(11-(3-hexyloxiran-2-yl)undec-6-enyl)thiazolidine-2,4-dione.

19. The pharmaceutical composition of claim 11, wherein the compound is (Z)-14-(hexyloxy)tetradec-5-enoate.

20. A method of treating a hypertension-related disease, said method comprising administering to a patient in need thereof a therapeutically effective amount of the compound of claim 1.

21. The method of claim 20, wherein the compound is selected from the group consisting of:
(Z)-1,3-dihydroxypropan-2-yl1 1-(nonyloxy)undec-8-enoate,
(Z)-2-(2-(2-hydroxyethoxy)ethoxy)ethyl1 1-(nonyloxy)undec-8-enoate,
(Z)-2-(11-(nonyloxy)undec-8-enamido)acetic acid,
sodium (Z)-10-(nonyloxy)dec-7-ene-1-sulfonate,
(Z)-2,3,4,5,6-pentahydroxyhexyl1 1-(nonyloxy)undec-8-enoate,
(Z)-5(11-(3-hexyloxiran-2-yl)undec-6-enyl)thiazolidine-2,4-dione, and
(Z)-14-(hexyloxy)tetradec-5-enoate.

22. The method of claim 20, wherein the compound is (Z)-2-(2-(2-hydroxyethoxy)ethoxy)ethyl1 1-(nonyloxy)undec-8-enoate.

23. The method of claim 20, wherein the hypertension-related disease involves endothelial dysfunction.

24. The method of claim 20, wherein the hypertension related disease is a renal or cardiovascular disease.

25. The method of claim 24 wherein the renal or cardiovascular disease is chosen from type 1 and type 2 diabetes, heptorenal syndrome, metabolic syndrome, insulin resistance syndrome, glomerulonephritis, hypertension, congestive heart failure, heart attack, hypertensive heart disease, atherosclerosis, coronary artery disease, angina, ischemia, ischemic stroke, Raynaud's disease, and renal disease.

27. The method of claim 20, wherein the hypertension-related disease is mediated by Angiotensin II.

26. The compound of claim 1, wherein the blood pressure is mediated by Angiotensin II.

* * * * *